United States Patent [19]

Kägi

[11] Patent Number: 4,775,756
[45] Date of Patent: Oct. 4, 1988

[54] 5-(4-AMINO-3,5-DIMETHOXYPHENYL)-5-HYDROXY-BARBITURIC ACID

[75] Inventor: Dieter Kägi, Basel, Switzerland

[73] Assignee: Hoffmann-La Roche Inc., Nutley, N.J.

[21] Appl. No.: 917,567

[22] Filed: Oct. 10, 1986

[30] Foreign Application Priority Data

Oct. 24, 1985 [CH] Switzerland .......................... 4592/85

[51] Int. Cl.$^4$ .......................................... C07D 239/62
[52] U.S. Cl. ..................... 544/302; 544/305
[58] Field of Search ................ 544/305, 300, 302

[56] References Cited

U.S. PATENT DOCUMENTS

| Re. 28,377 | 3/1975 | Samour et al. | 544/302 |
| 3,464,990 | 9/1969 | Brossi et al. | 544/302 |
| 3,784,547 | 1/1974 | Samour et al. | 544/302 |
| 3,925,386 | 12/1975 | Jager et al. | 544/302 |
| 4,292,312 | 9/1981 | Griffon | 544/298 |
| 4,454,320 | 6/1984 | Rajeckas et al. | 544/305 |
| 4,515,948 | 5/1985 | Kompis et al. | 544/325 |
| 4,628,056 | 12/1986 | Levitt et al. | 544/303 |

FOREIGN PATENT DOCUMENTS

| 54756 | 6/1982 | European Pat. Off. | 544/325 |
| 112174 | 6/1900 | Fed. Rep. of Germany . | |

OTHER PUBLICATIONS

King and Clark-Lewis, J. Chem. Soc. 3077 (1951).

Primary Examiner—Donald G. Daus
Assistant Examiner—Cecilia Shen
Attorney, Agent, or Firm—Jon S. Saxe; Bernard S. Leon; William G. Isgro

[57] ABSTRACT

The invention relates to substituted phenylbarbituric acids of the formula

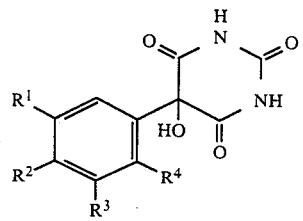

wherein $R^1$ and $R^3$, independently, are lower-alkoxy or lower-alkylthio; $R^2$ is lower-alkoxy, hydroxy or amino; and $R^4$ is hydrogen; or $R^1$ and $R^2$ are lower-alkoxy, $R^3$ is hydrogen and $R^4$ is lower-alkyl, which are prepared from correspondingly substituted benzene derivatives and alloxan. The compounds of formula I can be converted into substituted benzaldehydes which in turn are known intermediates in the preparation of pharmaceutically valuable benzylpyrimidines.

1 Claim, No Drawings

5-(4-AMINO-3,5-DIMETHOXYPHENYL)-5-HYDROXY-BARBITURIC ACID

BRIEF SUMMARY OF THE INVENTION

The invention relates to substituted phenylbarbituric acids of the formula

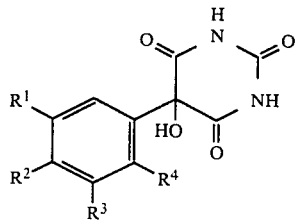

wherein $R^1$ and $R^3$, independently, are lower-alkoxy or lower-alkylthio; $R^2$ is lower-alkoxy, hydroxy or amino; and $R^4$ is hydrogen; or $R^1$ and $R^2$ are lower-alkoxy, $R^3$ is hydrogen and $R^4$ is lower-alkyl.

The compounds of formula I are useful as intermediates, as hereinafter described.

DETAILED DESCRIPTION OF THE INVENTION

The invention relates to substituted phenylbarbituric acids of the formula

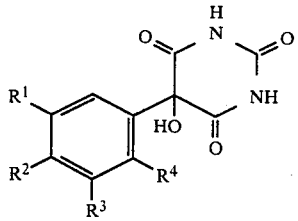

wherein $R^1$ and $R^3$, independently, are lower-alkoxy or lower-alkylthio; $R^2$ is lower-alkoxy, hydroxy or amino; and $R^4$ is hydrogen; or $R^1$ and $R^2$ are lower-alkoxy, $R^3$ is hydrogen and $R^4$ is lower-alkyl.

As used herein, lower alkoxy and lower alkyl preferably denote residues containing 1 to 7 carbon atoms, which may be straight-chain or branched. Examples of such residues are methoxy, ethoxy and propoxy, or methyl, ethyl and propyl, respectively. Preferred compounds of formula I are those in which $R^1$, $R^2$ and $R^3$ are methoxy and $R^4$ is hydrogen; or $R^1$ and $R^3$ are methoxy, $R^2$ is amino and $R^4$ is hydrogen; or $R^1$ and $R^2$ are methoxy, $R^3$ is hydrogen and $R^4$ is methyl.

The compounds of formula I can be prepared in accordance with the invention by reacting a corresponding compound of the formula

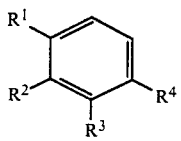

wherein $R^1$, $R^2$, $R^3$ and $R^4$ are as described above, with alloxan.

The reaction is conveniently carried out by adding a compound of formula II to an aqueous alloxan solution and intensively stirring the reaction mixture. If desired, a Friedel-Crafts catalyst, for example, zinc chloride, can be added to the reaction mixture. The resulting compound of formula I separates in solid form and can be removed by filtration and, if desired, purified by recrystallization.

The compounds of formula I can be used as intermediates in the preparation of antibacterially-active benzylpyrimidines, such as, trimethoprim. The present invention opens up a technically advantageous access to these compounds.

The compounds of formula I can be converted into benzyl pyrimidines such as those of the formula

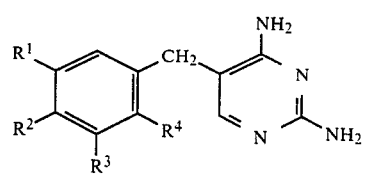

by a reaction sequence which comprises the steps of
(a) converting a compound of formula I into an aldehyde of the formula

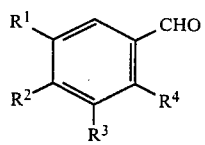

wherein $R^1$, $R^2$, $R^3$ and $R^4$ are as above,
(b) reacting the aldehyde of formula III with a substituted propionitrile of the formula

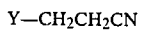

$$Y-CH_2CH_2CN \quad \quad IV$$

wherein Y is a leaving group,
to yield a compound of the formula

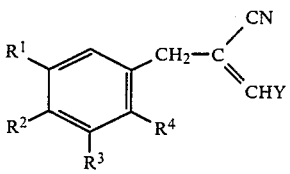

wherein $R^1$, $R^2$, $R^3$, $R^4$ and Y are as above
and
(c) reacting the compound of formula V with guanidine.

The compounds of formula I can be converted by hydrolysis, for example, by treatment with aqueous sulfuric acid while heating, neutralization of the hydrolysate and extraction with a suitable organic solvent, for example, ethyl acetate into aldehydes of the formula III.

In step (b) the aldehyde of formula III is reacted with a substituted propionitrile of formula V wherein Y is a leaving group.

Examples of suitable leaving groups are ether groups (e.g. lower alkoxy groups such as methoxy and ethoxy), thioether groups (e.g. alkylthio groups) or amino groups derived from primary or secondary amines. Examples of such amino groups are i) groups derived from primary aliphatic, aryl-aliphatic or aromatic amines such as lower alkylamino, benzylamino, and arylamino (e.g. naphthylamino), but especially phenyl-amino (anilino) which may carry in the phenyl ring one or more halogen, lower alkyl or lower alkoxy substituents, or ii) groups derived from secondary aliphatic, aromatic or heterocyclic amines such as N,N-di(lower alkyl)amino, N-(lower alkyl)-N-arylamino [e.g. N-methyl-N-phenylamino(N-methylanilino) which may carry in the phenyl ring one or more halogen, lower alkyl or lower alkoxy substituents], pyrrolidino, piperidono, piperazino and morpholino. An especially preferred amino leaving group is the anilino group.

The reaction of the aldehyde of formula III with a substituted propionitrile of formula IV is carried out in the presence of an alkali metal lower alkoxide, such as sodium methoxide, potassium ethoxide, etc. and a lower alkanol e.g., methanol ethanol, propanol, etc. The reaction temperature is not critical, but it is generally in the range of about 60° to about 140° C.

The reaction of a compound of formula V with guanidine is carried out in a solvent such as an alkanol (e.g. methanol or ethanol), dimethylformamide, dimethyl sulphoxide or N-methyl-pryazolone in the presence of an alkali metal lower alkoxide at a temperature in the approximate range of from 25° C. to 200° C., preferably at a temperature of from 50° C. to 170° C.

The Example which follows further illustrates the invention.

EXAMPLE 25 g of 2,6-dimethoxyaniline were added to a solution of 35 g of alloxan tetrahydrate in 120 ml of water. While stirring vigorously, the initially heterogeneous mixture changed after one hour into a brown solution from which grey crystals separated after a short time. The reaction mixture was stirred at room temperature for an additional 24 hours until dimethoxyaniline was no longer detectable according to thin-layer chromatography (cyclohexane/ethyl acetate/water=60:30:1). The reaction mixture was suction filtered, the residue on the suction filter was suspended with 4 portions of water to 80 ml and sucked dry. The solid was dried at 100°/16 mbar for 16 hours. There were obtained 44.2 g of 5-(4-amino-3,5-dimethoxyphenyl)-5-hydroxybarbituric acid as a light grey powder of m.p. 240°-243° (under decomposition). For purification, the powder can be recrystallized from 1-butanol, there being obtained a product of m.p. 242°-244° (decomposition).

The 5-(4-amino-3,5-dimethoxyphenyl)-5-hydroxybarbituric acid was converted as follows into the corresponding aldehyde of formula III:

28 ml of sulfuric acid (d=1.8; 0.45 mol) were heated to 120° while stirring and treated in one portion with 11.25 g of 5-(4-amino-3,5-dimethoxyphenyl)-5-hydroxybarbituric acid (0.038 mol). The mixture was stirred until evolution of gas was no longer observed (about 15-20 minutes) and then poured into a mixture of 140 g of ice and 140 g of water while stirring. Resinous polymerization products were separated by a filtration over a pad of 15 g of celite. While stirring and cooling, the filtrate was treated with 63.6 g of potassium carbonate powder until neutral. The aqueous suspension was extracted three times with 50 ml of ethyl acetate each time, the combined organic phases were dried over sodium sulfate and concentrated in water-jet vacuum. The residue was dried up to constant weight in a high vacuum. There was obtained 6.36 of crude 4-amino-3,5-dimethoxybenzaldehyde as a yellow oil which solidified on standing (mp=94°-96° C.). The purity determined by gas chromatography was 96%. 4-amino-3,5-dimethoxybenzaldehyde was converted into 2,4diamino-5-(4-amino-3,5-dimethoxybenzyl)pyrimidine as follows:

A mixture of 8.1 g (0.15 mol) of sodium methylate and 21.0 g (0.15 mol) of B-morpholino-propionitrile in 100 ml of absolute dimethyl sulphoxide was treated during 10 minutes with a solution of 18.1 g (0.1 mol) of 4-amino-3,5-dimethoxy-benzaldehyde in 50 ml of absolute dimethyl sulphoxide while stirring at 60° C. After stirring at 60° C. for 30 minutes, the mixture was poured into 1.5 liters of water and the precipitate was extracted with two 1 liter portions of ethyl acetate. The ethyl acetate extract was washed with two 500 ml portions of water, dried over magnesium sulphate and evaporated in vacuo. There were obtained 35 g of crystalline residue which were triturated with 40 ml of alcohol and, after standing for 2 hours at 4° C., filtered off under suction, washed with a small amount of ice-cold alcohol and dried. There was obtained α-(4-amino-3,5-dimethoxy-benzyl)-β-morpholino -acrylonitrile of melting point 128°-129° C.

A mixture of 6.5 g of sodium methylate, 21.6 g of guanidine carbonate and 12.8 g of α-(4-amino-3,5-dimethoxy-benzyl)-β-morpholino - acrylonitrile in 120 ml of absolute dimethyl sulphoxide was stirred at 120° C. for 60 hours. Subsequently, the mixture was diluted with 1.2 liters of water and extracted with two 2 liter portions of ethyl acetate. The ethyl acetatae extract was washed with two 1 liter portions of water, dried over magnesium sulphate and evaporated in vacuo. After recrystallisation of the residue from methanol, there was obtained 2,4-diamino-5-(4-amino-3,5-dimethoxybenzyl)-pyrimidine of melting point 215°-216° C.

I claim:

1. 5-(4-amino-3,5-dimethoxyphenyl)-5-hydroxy-barbituric acid.

* * * * *